US011517460B2

(12) United States Patent
Storbeck et al.

(10) Patent No.: US 11,517,460 B2
(45) Date of Patent: Dec. 6, 2022

(54) DEVICES AND METHODS FOR MODULATING INTESTINAL FLOW

(71) Applicants: Boston Scientific Scimed, Inc., Maple Grove, MN (US); Lifespan Corporation, Providence, RI (US)

(72) Inventors: Gene T. Storbeck, Millis, MA (US); John A. Hingston, Framingham, MA (US); Selina M. Mello, St. Louis Park, MN (US); Jeri Ann Hiller, Westford, MA (US); Kathleen Corcoran, Watertown, MA (US); Kali L. Manning, Providence, RI (US); Gary Dean Roye, Cranston, RI (US); Sivamainthan Vithiananthan, Sharon, MA (US); Beth Ryder, Warwick, RI (US)

(73) Assignees: Boston Scientific Scimed, Inc., Maple Grove, MN (US); Lifespan Corporation, Providence, RI (US)

( * ) Notice: Subject to any disclaimer, the term of this patent is extended or adjusted under 35 U.S.C. 154(b) by 29 days.

(21) Appl. No.: 16/941,951

(22) Filed: Jul. 29, 2020

(65) Prior Publication Data
US 2020/0352768 A1   Nov. 12, 2020

Related U.S. Application Data

(63) Continuation of application No. 15/790,163, filed on Oct. 23, 2017, now Pat. No. 10,758,389.

(60) Provisional application No. 62/411,839, filed on Oct. 24, 2016.

(51) Int. Cl.
*A61F 5/00* (2006.01)
*A61F 2/04* (2013.01)

(52) U.S. Cl.
CPC .............. *A61F 5/0079* (2013.01); *A61F 2/04* (2013.01); *A61F 5/0086* (2013.01); *A61F 2002/044* (2013.01); *A61F 2002/045* (2013.01); *A61F 2250/0003* (2013.01)

(58) Field of Classification Search
CPC ............ A61F 5/0003–0096; A61F 2/04; A61F 2250/0003; A61F 2002/044; A61F 2002/045
See application file for complete search history.

(56) References Cited

U.S. PATENT DOCUMENTS

| | | | |
|---|---|---|---|
| 7,771,382 B2 | 8/2010 | Levine et al. | |
| 8,211,186 B2 | 7/2012 | Belhe et al. | |
| 2006/0161139 A1* | 7/2006 | Levine | A61F 5/0079 606/1 |
| 2011/0190905 A1 | 8/2011 | Behan | |
| 2012/0310138 A1 | 12/2012 | Behan | |
| 2013/0165842 A1* | 6/2013 | Binmoeller | A61F 5/0079 604/9 |
| 2015/0065939 A1* | 3/2015 | Harris | A61F 5/0076 604/8 |

(Continued)

*Primary Examiner* — Brian A Dukert
*Assistant Examiner* — Rebecca Lynee Zimmerman
(74) *Attorney, Agent, or Firm* — Bookoff McAndrews, PLLC

(57) ABSTRACT

A device for implanting in a gastrointestinal system of a patient may include an elongate flow modulator configured to be inserted in an intestine, wherein the flow modulator defines an enclosed interior space to hold a fill material.

17 Claims, 2 Drawing Sheets

(56) References Cited

U.S. PATENT DOCUMENTS

2016/0022461 A1* 1/2016 Errico .................. A61F 5/0076
604/8
2016/0058914 A1 3/2016 Bangera et al.

* cited by examiner

DEVICES AND METHODS FOR MODULATING INTESTINAL FLOW

CROSS-REFERENCE TO RELATED APPLICATION(S)

This patent application is a continuation of U.S. application Ser. No. 15/790,163, filed on Oct. 23, 2017, which claims the benefit under 35 U.S.C. § 119 to U.S. Provisional Patent Application No. 62/411,839, filed on Oct. 24, 2016, all of which are incorporated herein by reference in their entireties.

TECHNICAL FIELD

Embodiments of the present disclosure relate generally to devices and methods for modulating the flow of food in the gastrointestinal tract of a patient.

BACKGROUND

Current methods for obesity treatment include surgery to alter the anatomy of the patient or the implantation of devices in the gastrointestinal system to increase feelings of satiety and/or reduce absorption of nutrients. For example, a portion of the stomach may be removed in a sleeve gastrectomy procedure, or space occupiers may be placed in the stomach to reduce the volume of the stomach and cause the patient to feel full. Another type of treatment may include implanting intestinal sleeves in the intestine to prevent chyme from contacting a portion of the intestine.

SUMMARY

Examples of the present disclosure relate to, among other things, devices and methods for modulating the flow of chyme through the intestine, thereby reducing the absorption of nutrients in the gastrointestinal system. Each of the examples disclosed herein may include one or more of the features described in connection with any of the other disclosed embodiments.

In one example, a device for implanting in a gastrointestinal system of a patient may include an elongate flow modulator configured to be inserted in an intestine, wherein the flow modulator defines an enclosed interior space to hold a fill material.

The device may additionally or alternatively include one or more of the following features: a dimension of the flow modulator may be configured to be adjustable after being inserted in the intestine by modifying an amount of the fill material inside the interior space; a cross-sectional area of a first region of the flow modulator may be larger than a cross-sectional area of a second region of the flow modulator; the flow modulator may be more compliant in an axial direction than in a radial direction; the flow modulator may include preformed curves along a length of the flow modulator; the fill material may include at least one of air, foam, hydrogel, cross-linked materials, or associative thickeners; the enclosed interior space may be surrounded by a continuous outer boundary that includes at least one of a self-sealing material, a valve, or a Luer lock; the device may further include an anchor coupled to the flow modulator; and the device may further include a sleeve configured to be positioned in the intestine, wherein the flow modulator is configured to be positioned within a lumen of the sleeve.

In another example, a device for implanting in a gastrointestinal system of a patient may include an anchor configured to exert radially outward pressure on a wall of the gastrointestinal system; an elongate space occupier coupled to the anchor; and a sleeve coupled to at least one of the anchor or the elongate space occupier, wherein the space occupier is positioned in a lumen of the sleeve.

The device may additionally or alternatively include one or more of the following features: the anchor may include a frame configured to be positioned in a distal portion of a stomach; the anchor may include a valve configured to be positioned within a pylorus; the elongate space occupier may define an enclosed interior space; the enclosed interior space may be surrounded by a continuous outer boundary that includes at least one of a self-sealing material, a valve, or a Luer lock; and the device may further include a ring configured to be implanted exterior to and around a pylorus of the patient.

In yet another example, a method for implanting a device in a gastrointestinal system of a patient may include inserting a space occupier into an intestine of the patient; inserting an anchor into the patient and positioning the anchor proximal to the space occupier; and expanding the space occupier by inserting a fill material into an interior space of the space occupier, wherein the space occupier holds the fill material within the interior space.

The method may additionally or alternatively include one or more of the following features or steps: the method may further comprise inserting a sleeve into the intestine of the patient, wherein the space occupier is positioned inside a lumen of the sleeve; the sleeve may include a frame and a membrane; inserting the fill material may include inserting a needle through a self-sealing material of the space occupier; and the anchor may include a stent, and inserting the anchor into the patient may include positioning the stent in a distal portion of a stomach.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to devices and methods for modulating the flow of chyme through a patient's intestinal tract to reduce the absorption of nutrients. As used herein, "chyme" may refer to any substance that enters the intestine from the stomach. In one example, a flow modulator may include a balloon or other device having an adjustable volume. The flow modulator may be placed in the patient's intestinal tract. The flow modulator may be anchored by any suitable method, and it may be used in conjunction with an intestinal sleeve or other devices used to treat obesity.

Figure 1:
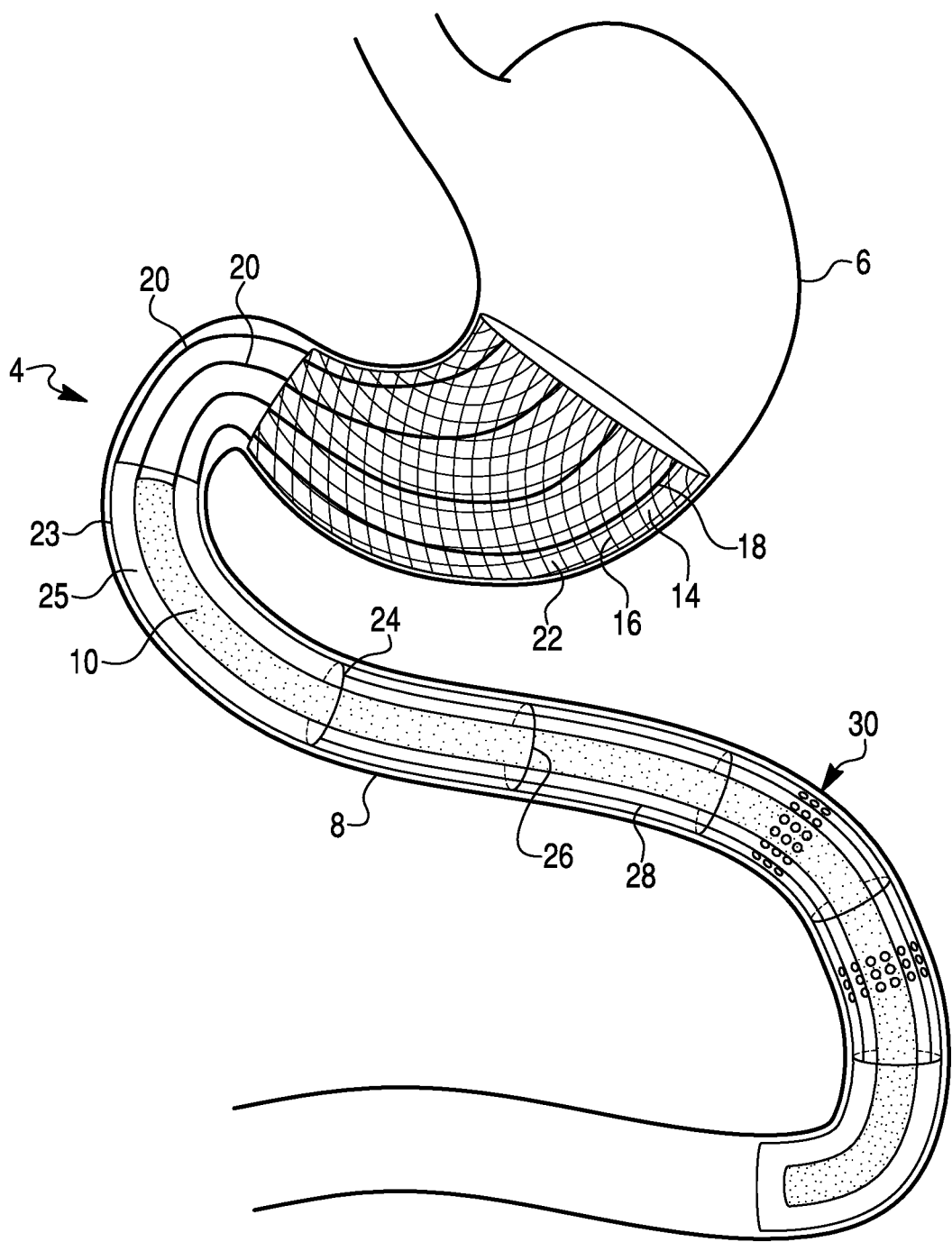
FIG. 1 illustrates a flow modulator implanted in an intestine and an anchor positioned in a stomach, according to an exemplary embodiment.

Referring to FIG. 1, a device 4 may include a flow modulator 10 positioned in an intestine 8 of a patient. Flow modulator 10 may be coupled by one or more tethers 20 to an anchor 14, which may be positioned in the stomach 6 of a patient. Device 4 may further include a sleeve 23 coupled to anchor 14 by one or more additional tethers 20. Additionally or alternatively, sleeve 23 may be coupled directly to flow modulator 10.

Flow modulator 10 may be an elongate member configured to occupy space within intestine 8. By occupying space within intestine 8, chyme may be forced to flow through smaller cross-sectional areas around flow modulator 10. Although there is less room for flow of chyme, the peristaltic action of intestine 8 may remain the same. Accordingly, with flow modulator 10 in intestine 8, the chyme may flow faster past regions of intestine 8, which may reduce absorption of nutrients and aid in weight loss. In addition to influencing the rate of flow through intestine 8, flow modulator 10 may increase the amount of time food is retained in stomach 6. By keeping food in stomach 6 longer, the patient may feel full earlier and/or longer.

Flow modulator 10 may be a balloon that is inflated or filled with a liquid, semi-solid, or solid fill material. Flow modulator 10 may define an interior space. Once fill material has been inserted into flow modulator 10, flow modulator 10 may form a continuous outer boundary to hold the fill material within the interior space. In some examples, the fill material may be low in density and immobile within the modulator, to prevent the material from collecting at a distal end of flow modulator 10. Exemplary fill materials may include air, saline solution, foams, hydrogels, cross-linked materials, associative thickeners, etc. The fill material may begin as a liquid and transform to a semi-solid or solid material after flow modulator 10 has been filled, such as when the fill material reaches a certain temperature. The fill material may further be configured to transform from a semi-solid or solid material back to a liquid for removal from flow modulator 10.

Flow modulator 10 may be adjustable in diameter or length by increasing or decreasing the amount of fill material injected into flow modulator 10. For example, if flow modulator 10 includes a semi-compliant material, a larger amount of fill material would cause flow modulator 10 to have a larger diameter than it would with a smaller amount of fill material. The flow modulator 10 may be more compliant in a radial direction than in an axial direction, so that increasing the amount of fill material may cause the flow modulator 10 to widen, and decreasing the amount of fill material may cause the flow modulator 10 to become more narrow. In another example, flow modulator 10 may be less compliant or non-compliant in a radial direction, and more compliant in an axial direction. Accordingly, increasing the amount of fill material may cause flow modulator 10 to lengthen, while reducing the amount of fill material may cause flow modulator 10 to shorten.

Flow modulator 10 may have a generally circular cross-section, although flow modulator 10 may have any shape. Flow modulator 10 may have a length between 0.6-1.2 meters (2-4 feet) or between 0.9-1.2 meters (3-4 feet), although the flow modulator 10 may have a length less than 0.6 meters or greater than 1.2 meters in other examples. In some examples, flow modulator 10 may have a diameter between 10-30 mm, between 10-20 mm, or between 20-30 mm, although the diameter may be less than 10 mm or greater than 30 mm in other examples. In one example, flow modulator 10 may include preformed curves to aid flow modulator 10 in conforming to the tortuous path of intestine 8. In another example, flow modulator 10 may include cross-sections having different areas. Different sized cross-sections may be useful to modify the absorption of nutrients along intestine 8. For example, to increase absorption of a certain nutrient in a region of intestine 8, the cross-section of flow modulator 10 may be reduced along that region. The chyme may then have a longer residence time in that region, and nutrient absorption may be increased. In other regions that absorb, for example, fats, the cross-sectional area of flow modulator 10 may be increased. The increased area in that region may reduce the residence time of chyme in that region and consequently reduce the patient's absorption of fats.

In some examples, flow modulator 10 may be coated with materials to influence nutrient absorption. Some coatings may increase the flow of chyme along flow modulator 10, and some coatings (e.g., hydrophilic coatings) may elute drugs to alter absorption rates.

Flow modulator 10 may be inflated or deflated using any suitable mechanism. In one example, a portion of flow modulator 10 may include a self-sealing material, such as silicone covered by a layer of PTFE. The self-sealing material may be easily punctured by a needle, but may self-seal once the needle is removed. The needle may be used to inject or remove material from flow modulator 10. The self-sealing material may be included in a proximal section of flow modulator 10 to allow the size of flow modulator 10 to be adjusted either prior to implantation or after flow modulator 10 has been implanted and positioned in intestine 8. In another example, flow modulator 10 may include a valve. The valve may allow material to flow into and fill flow modulator 10, but may prevent material from flowing out of flow modulator 10 (unless being actively removed by a user). In yet another example, flow modulator 10 may include a Luer lock or other mechanism that serves as a connection between two fluid-carrying devices. The Luer lock may be configured to receive a device to allow fluid to be injected into or removed from flow modulator 10. Finally, in another example, flow modulator 10 may include a tube extending from its proximal end. Flow modulator 10 may be inserted into a patient and filled via the tube. Once the desired inflation is reached, the tube may be heat sealed adjacent to the proximal end of flow modulator 10. The tube may then be removed from the patient, leaving the inflated flow modulator 10 within the patient.

Device 4 may optionally include a sleeve 23 coupled to anchor 14 by one or more tethers 20. Additionally or alternatively, sleeve 23 may be coupled to flow modulator 10 by tethers, wires, or other mechanisms that would allow chyme to pass between the sleeve 23 and flow modulator 10. Sleeve 23 may be positioned in intestine 8. The sleeve 23 may include a lumen, and flow modulator 10 may be positioned within the lumen.

Sleeve 23 may include a liner 25 and a frame 24. The sleeve 23 may reduce the absorption of nutrients by reducing contact between chyme and the intestinal wall of the patient. Liner 25 may include silicone, liquid silicone rubber, polytetrafluoroethylene (PTFE), polyethylene terephthalate (PET), ultra-high-molecular-weight polyethylene (UHMWPE) or any biomaterial resistant to the stomach acid environment. In one example, liner 25 and/or frame 24 may be bioabsorbable, biodegradable, or bioresorbable. Sleeve 23 therefore may degrade after a certain period of time and either bioabsorb or break apart and be passed naturally, leaving flow modulator 10 within the patient.

In one example, liner 25 may include porous regions 30 having a material that is more permeable than adjacent portions of the liner 12, as described in U.S. Patent Application No. 62/256,380, titled "Devices and Methods for Reducing Absorption," filed Nov. 17, 2015, and incorporated by reference herein in its entirety. Although the liner 25 may inhibit absorption of nutrients, the porous regions 30 may allow absorption in key locations to meet the patient's nutritional needs.

The porous regions 30 may include a mesh-like material that includes openings that would allow some chyme to pass through the openings and/or allow digestive fluids or hormones to pass through the openings into the sleeve. For purposes of this disclosure, the term "pore" will be used to refer to an opening in the liner 25 and may include micropores. The portions of the sleeve adjacent or between the porous regions 30 may be impermeable, or may be permeable to a lesser degree than the porous regions. In various examples, the porous regions 30 may align with one or more regions of intestine 8 that either absorb certain nutrients (e.g., $Fe^{++}$, $Ca^{++}$, $Mg^{++}$, water soluble vitamins, or fat soluble vitamins) or produce hormones that aid in digestion (e.g., GIP, CCK, GLP-1, oxyntomodulin, PYY). The porous regions 30 may allow chyme from the interior of sleeve 23 to exit sleeve 23 and contact the intestinal wall, where nutrients may be absorbed. The porous regions 30 may additionally allow digestive fluids to enter the sleeve 23 in regions that produce digestive hormones. The digestive hormones may interact with the chyme inside the sleeve 23, making the nutrients available for absorption if the chyme exits the sleeve 23 via a porous region 30. In one example, a porous region 30 may selectively allow certain nutrients to pass through the liner 25 of sleeve 23.

Sleeves 23 having variable lengths may be manufactured to appropriately fit the intestines of different patients so that the appropriate sleeve sections (e.g., porous regions 30 or impermeable regions) are adjacent desired regions of the patient's intestine 8 for desired absorption of nutrients and/or entrance of digestive fluids/hormones into sleeve 23. For example, to optimize nutrient absorption and/or entrance of digestive fluids/hormones, a sleeve 23 for a patient having a shorter intestinal length may include porous regions 30 that are closer together, and a sleeve 23 for a patient having a longer intestine may include porous regions 30 that are farther apart.

Additionally or alternatively, sleeve 23 may include a frame 24, such as the frame described in Application No. 62/256,380, incorporated by reference herein, that may exert radially outward pressure on intestine 8. The frame 24 may affect peristalsis to, for example, slow the passage of chyme through intestine 8. The frame 24 may be useful in positioning the liner 25 adjacent to the wall of intestine 8. The frame 24 and liner 25 may be integrally formed, with the liner 25 molded around all of or portions of the frame 24. The frame 24, and therefore the sleeve 23, may be self-expandable. In one example, the frame 24 may be a braided wire or material, similar to a stent, that may reduce the tendency of the sleeve 23 to fold. In another example, the frame 24 may include a plurality of circumferential loops 26 and connectors 28 joining at least some of the circumferential loops 26. The circumferential loops 26 may extend 360° around a circumference of sleeve 23. The frame 24, however, may be any suitable material or configuration sufficient to give structural integrity to liner 25. The material of the frame 24 may be biocompatible. For example, the frame 24 may be nitinol, stainless steel, permanent polymers like PET, etc.

Referring to FIG. 1, anchor 14 may be similar to a stent. Anchor 14 may be shaped to conform to a distal portion of stomach 6 and may exert a radially outward force to maintain its position in stomach 6. Anchor 14 may additionally or alternatively be secured to stomach 6 by any suitable connection mechanism, such as sutures or serrated teeth on an outer surface of anchor 14. Anchor 14 may prevent flow modulator 10 and sleeve 23 from migrating distally within intestine 8. In one example, anchor 14 may include a frame 16 and a membrane 22 covering the frame 16 (e.g., a covered stent). In another example, the anchor 14 may include a bare frame 16 without a membrane (e.g., a bare stent). The frame 16 and membrane 22 may include any of the features described above in connection with the frame 24 and liner 25 of the sleeve 23. The anchor 14 may include a braided design. The anchor 14 may be self-expandable, like nitinol stents. In an alternative example, the anchor 14 may be expanded by an expansion device, such as a balloon inserted within an interior space of anchor 14. Once implanted in a patient, the anchor 14 may exert a radially outward force on the stomach wall to prevent distal migration of flow modulator 10 and sleeve 23.

The radially outward force exerted by anchor 14 may resist peristaltic wave forces that exert pressure to open the pyloric sphincter, which is distal to anchor 14 in an example. With the anchor 14 in place, the pyloric sphincter may open less frequently and/or to a lesser extent. Accordingly, less food may exit the stomach 6 with each peristaltic wave generated. The anchor 14 may therefore inhibit gastric emptying, which may increase satiety and promote weight loss.

Figure 2:
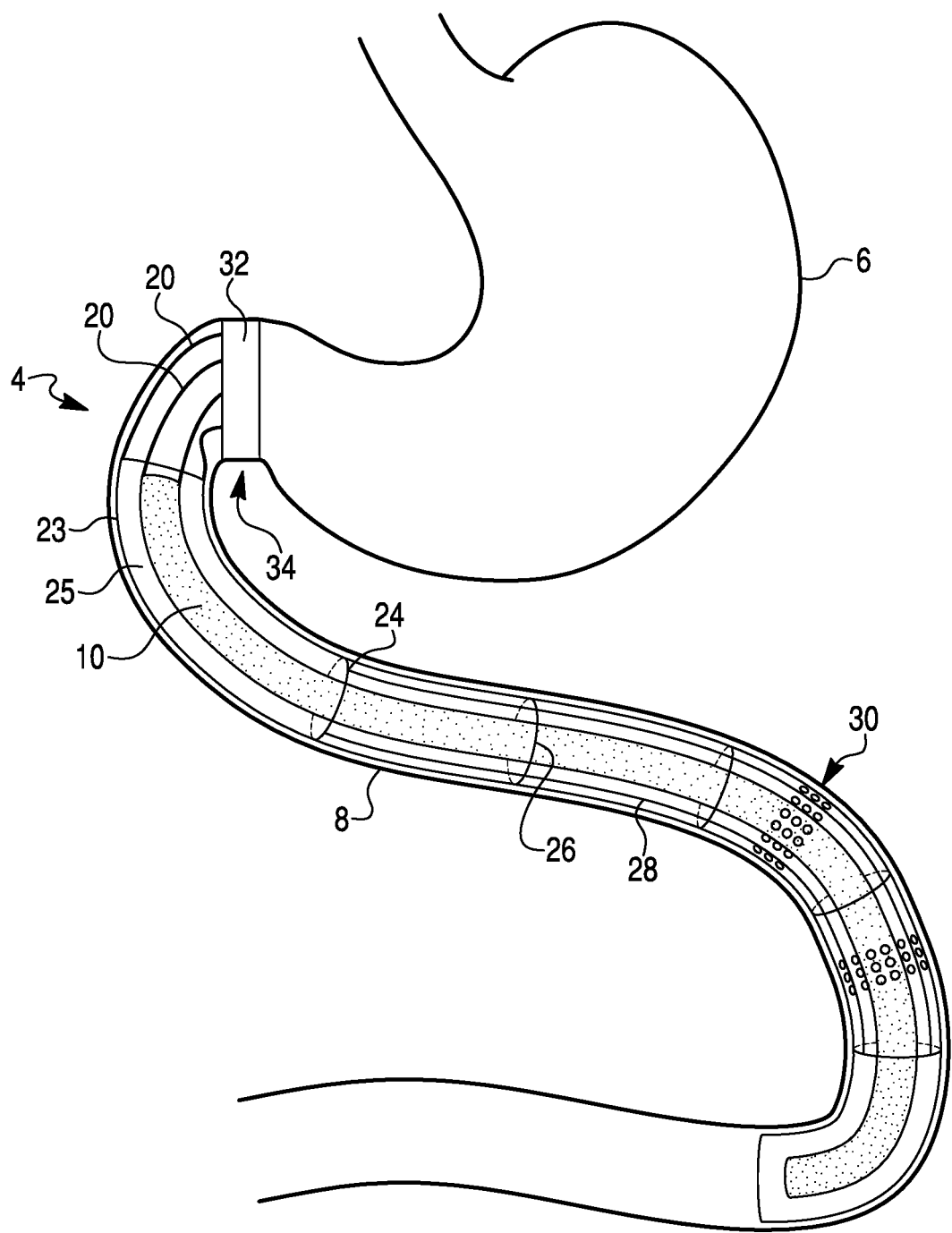
FIG. 2 illustrates a flow modulator implanted in an intestine and an anchor positioned in a pylorus, according to an exemplary embodiment.

Referring to FIG. 2, an alternative embodiment of an anchor may be positioned in a patient's pylorus 34 and may be secured to flow modulator 10 and/or sleeve 23 by one or more tethers 20. The anchor 32 may include a circumferential ring. The anchor 32 may be secured to the patient using any suitable connection mechanism, such as sutures or serrated teeth. Like anchor 14, anchor 32 may prevent flow modulator 10 and liner 12 from migrating distally within intestine 8. At least a portion of anchor 32 may be radially expandable, and anchor 32 may act as a pyloric valve replacement. A central portion of anchor 32 may therefore include a valve that allows food to pass from stomach 6 to intestine 8 but may prevent food from passing from intestine 8 to stomach 6. The valve portion of the anchor 32 may require greater pressure to be opened than the patient's natural pyloric sphincter. Therefore, less food may exit stomach 6 with each peristaltic wave, and similarly to anchor 14, anchor 32 may inhibit gastric emptying to increase satiety and promote weight loss. In one example, anchor 32 may be implanted within the pyloric canal.

In an alternative example, anchor 32 may be implanted exterior to the pyloric sphincter (e.g., outside of and surrounding the pylorus, around an exterior of the gastrointestinal wall in an example). Anchor 32 in this example may be a ring having a dimension sufficient to "squeeze" the pyloric canal to a greater extent than the patient's natural pyloric sphincter. Anchor 32 may include an elongated member that is movable between an elongated configuration for implantation and a ring configuration, in which the two ends of the elongated member have been connected to each other to form a ring around the pylorus. The anchor 32 may be radially expandable when peristaltic action pushes the sphincter open, allowing food to pass from stomach 6 to intestine 8 but inhibiting gastric emptying to a greater extent than the patient's natural anatomy. If anchor 32 is implanted exterior to the pylorus, flow modulator 10 and/or sleeve 23 may be secured to the intestine using sutures, dumbbell shaped anchors passed through tissue plications, or any other suitable methods/devices. Alternatively, an exterior anchor 32 may be used in combination with anchor 14, and flow modulator 10 and/or sleeve 23 may be coupled to anchor 14.

Device 4, including one or more of anchor 14/anchor 32, flow modulator 10, and sleeve 23, may be implanted into a patient's stomach and intestine transorally through a tubular sheath, and an endoscope may be used to visualize placement. Both flow modulator 10 and sleeve 23 may be positioned distal to pylorus 34, with flow modulator 10 inside the lumen of sleeve 23. One of the above-described methods of inflation may then be used to expand flow modulator 10. Anchor 14 may be positioned in a distal portion of stomach 6, or alternatively, anchor 32 may be positioned in the patient's pylorus 34. Anchor 14 or 32 may self-expand upon exiting the tubular sheath. In another example, anchor 32 may be positioned exterior to the patient's pylorus 34 through a minimally-invasive laparoscopic procedure. Flow modulator 10 may be removed from the patient by removing the fill material and either pulling flow modulator 10 proximally through the stomach and esophagus or allowing flow modulator 10 to pass naturally from the patient.

Several features of device 4 may induce weight loss in a patient. By occupying space, flow modulator 10 may increase the speed that chyme flows past the intestinal wall, reducing absorption of nutrients. If flow modulator 10 includes variable cross-sections, nutrient absorption may be modified along different portions of intestine 8. In addition, coatings on flow modulator 10 may affect the propulsion of chyme, which may reduce absorption. Sleeve 23 may further reduce absorption of nutrients, while the porous regions 30 may allow chyme to pass through the sleeve 23 at select locations to prevent malnutrition. Anchors 14 and 32 may slow gastric emptying by interfering with peristaltic action and/or increasing the pressure required to open the pylorus 34, thereby increasing satiety of the patient.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A device for implanting in a gastrointestinal system of a patient, comprising:
   an anchor having a circumferential surface, wherein the circumferential surface of the anchor is configured to exert a radially outward force in at least two opposing directions on a wall of a gastrointestinal tract;
   a flow modulator configured to be inserted in an intestine, wherein the flow modulator defines an enclosed interior space to hold a fill material, wherein the flow modulator is coupled to the anchor such that a proximalmost end of the flow modulator is distal to the anchor and there is a gap between the proximalmost end of the flow modulator and the anchor along a longitudinal axis of the flow modulator, wherein the flow modulator includes preformed curves along a length of the flow modulator; and
   a sleeve including a lumen defined by a membrane;
   wherein the flow modulator is positioned in the lumen, and the device is configured to be positioned in an intestine, such that chyme may flow around the flow modulator and the flow modulator exerts no influence on a peristaltic action of the intestine, and wherein the sleeve is coupled to the anchor such that a proximalmost end of the sleeve is distal to the anchor and there is a gap between the proximalmost end of the sleeve and the anchor along a longitudinal axis of the sleeve.

2. The device of claim 1, wherein a dimension of the flow modulator is configured to be adjustable after being inserted in the intestine by modifying an amount of the fill material inside the interior space.

3. The device of claim 1, wherein a cross-sectional area of a first region of the flow modulator is larger than a cross-sectional area of a second region of the flow modulator.

4. The device of claim 1, wherein the fill material includes at least one of air, saline solution, foam, hydrogel, cross-linked materials, or associative thickeners.

5. The device of claim 1, wherein the enclosed interior space is surrounded by a continuous outer boundary that includes at least one of a self-sealing material, a valve, or a Luer lock.

6. A device for implanting in a gastrointestinal system of a patient, comprising:
   an anchor including a stent, wherein a circumferential surface of the stent is configured to exert a radially outward force on a wall of a gastrointestinal tract in at least two opposing directions;
   a flow modulator configured to be inserted in an intestine, wherein the flow modulator defines an enclosed interior space to hold a fill material, wherein a cross-sectional area of a first region of the flow modulator is larger than a cross-sectional area of a second region of the flow modulator; and
   a sleeve including a lumen defined by a membrane; wherein the flow modulator is positioned in the lumen, and the device is configured to be positioned in an intestine, such that chyme may flow around the flow modulator and the flow modulator does not influence a peristaltic action of the intestine;
   wherein the flow modulator is coupled to the stent by a first tether extending between a proximalmost end of the flow modulator and the stent, and wherein the sleeve is coupled to the stent by a second tether extending between a proximalmost end of the sleeve and the stent.

7. The device of claim 6, wherein there is a gap between the proximalmost end of the flow modulator and the anchor along a longitudinal axis of the flow modulator, and wherein there is a gap between the proximalmost end of the sleeve and the anchor along a longitudinal axis of the sleeve.

8. The device of claim 6, wherein a dimension of the flow modulator is configured to be adjustable after being inserted in the intestine by modifying an amount of the fill material inside the interior space.

9. The device of claim 6, wherein the fill material includes at least one of air, saline solution, foam, hydrogel, cross-linked materials, or associative thickeners.

10. The device of claim 6, wherein the enclosed interior space is surrounded by a continuous outer boundary that includes at least one of a self-sealing material, a valve, or a Luer lock.

11. The device of claim 6, wherein the flow modulator is more compliant in a radial direction than in an axial direction.

12. A device for implanting in a gastrointestinal system of a patient, comprising:
- an anchor having a circumferential surface, wherein the circumferential surface of the anchor is configured to exert a radially outward force on a wall of a gastrointestinal tract in at least two opposing directions;
- a flow modulator configured to be inserted in an intestine such that the flow modulator exerts no influence on a peristaltic action of the intestine and chyme may flow around the flow modulator, wherein the flow modulator defines an enclosed interior space to hold a fill material, wherein the flow modulator is coupled to the anchor such that a proximalmost end of the flow modulator is distal to the anchor and there is a gap between the proximalmost end of the flow modulator and the anchor along a longitudinal axis of the flow modulator, wherein a cross-sectional area of a first region of the flow modulator is larger than a cross-sectional area of a second region of the flow modulator; and
- a tether extending between the flow modulator and the anchor.

13. The device of claim 12, further comprising a sleeve including a lumen defined by a membrane, wherein the flow modulator is positioned in the lumen, wherein the sleeve is coupled to the anchor such that a proximalmost end of the sleeve is distal to the anchor, and wherein there is a gap between the proximalmost end of the sleeve and the anchor along a longitudinal axis of the sleeve.

14. The device of claim 12, wherein a dimension of the flow modulator is configured to be adjustable after being inserted in the intestine by modifying an amount of the fill material inside the interior space.

15. The device of claim 12, wherein the fill material includes at least one of air, saline solution, foam, hydrogel, cross-linked materials, or associative thickeners.

16. The device of claim 12, wherein the enclosed interior space is surrounded by a continuous outer boundary that includes at least one of a self-sealing material, a valve, or a Luer lock.

17. The device of claim 12, wherein the flow modulator is more compliant in a radial direction than in an axial direction.

* * * * *